(12) United States Patent
Ikonte et al.

(10) Patent No.: US 7,718,201 B2
(45) Date of Patent: May 18, 2010

(54) METHOD OF INDUCING LIVER PHASE II ENZYMES

(75) Inventors: Chioma Jane Ikonte, Corona, CA (US); Michael Huang, Guangzhou (CN); Cherie L. Hacker, Comstock Park, MI (US); Silvia R. da Costa, Redondo Beach, CA (US); Paul D. Johnson, Nuevo, CA (US); Amitabh Chandra, Ada, MI (US); Christine M. Paganelli, Wyoming, MI (US); Ruo G. Huang, Long Beach, CA (US)

(73) Assignee: Access Business Group International LLC, Ada, MI (US)

( * ) Notice: Subject to any disclaimer, the term of this patent is extended or adjusted under 35 U.S.C. 154(b) by 33 days.

(21) Appl. No.: 12/218,585

(22) Filed: Jul. 16, 2008

(65) Prior Publication Data

US 2009/0011054 A1 Jan. 8, 2009

Related U.S. Application Data

(62) Division of application No. 11/274,618, filed on Nov. 15, 2005, now Pat. No. 7,419,689.

(51) Int. Cl.
*A61K 35/78* (2006.01)
(52) U.S. Cl. .................................... 424/728
(58) Field of Classification Search ................ 424/728, 424/725, 773, 777, 779; 514/893
See application file for complete search history.

(56) References Cited

U.S. PATENT DOCUMENTS 7,419,689 B2 * 9/2008 Ikonte et al. ................ 424/728

* cited by examiner

*Primary Examiner*—Ralph Gitomer
(74) *Attorney, Agent, or Firm*—Steven E. Merritt; Alticor Inc.

(57) ABSTRACT

The present invention is directed to plant based formulations for improving liver health by protecting the liver from alcohol and chemical insults and/or by inducing phase II enzymes. Formulations according to the present invention include wasabi root fiber powder, artichoke leaf extract, asparagus dehydrate, kudzu root extract, oregano extract, schisandra berry extract, notoginseng (ethanol extract of *Panax notoginseng* root), sanchi (water extracts from *Panax notoginseng* root), Gegen root extract (*Pueraria omeiensis*), spinach dehydrate, or combinations thereof.

4 Claims, 4 Drawing Sheets

METHOD OF INDUCING LIVER PHASE II ENZYMES

CROSS REFERENCE TO RELATED APPLICATION

This application is a divisional of U.S. patent application Ser. No. 11/274,618, filed Nov. 15, 2005 (now U.S. Pat. No. 7,419,689), hereby incorporated by reference.

BACKGROUND OF THE INVENTION

The present invention is directed to unique formulations of plant-based extracts that work synergistically to aid in good liver health. More specifically, the present invention relates to a unique formulation of plant-based extracts that assist in protecting the liver from alcohol and chemically induced damage.

The liver is one of the hardest working organs in the body. Good liver function is important for balanced hormone levels, weight control and maintenance, cholesterol levels, skin health and general health. The liver serves as the body's clearing house and is responsible for the metabolism of a number of substances, including alcohol, and plays an important role in the detoxification of toxins in the body. Phase II enzymes are part of this detoxification process because they aid in the removal of potential carcinogens from the body. As a result of its function in the body, the liver is under constant attack and prone to damage from environmental toxins, impurities, alcohol, prescription and over-the-counter drugs. Many hepatotoxicants such as carbon tetrachloride, nitrosamines, and polycyclic aromatic hydrocarbons are metabolically activated by liver enzymes to form reactive, toxic metabolites that cause injury to the liver in humans.

Thus, a formulation of plant-based extracts that aids in protecting the liver against alcohol and carbon tetrachloride insults would be useful. Additionally, a plant-based formulation that works to induce phase II enzymes responsible for detoxifying the liver would be useful.

SUMMARY OF THE INVENTION

The present invention is directed to unique formulations that improve liver health by working to protect the liver from carbon tetrachloride and alcohol insults. Formulations of the present invention have shown strong protective abilities on human liver cells as measured by indices such as 3-(4,5-dimethylthiazolyl-2)-2,5-diphenyltetrazolium bromide, which is a tetrazolium salt, ("MTT") and lactase dehydrogenase ("LDH"). In addition, these extracts and their combinations show strong phase II enzyme induction activity. The phase II enzyme induction assay measures a sample's ability to induce quinone reductase (a phase II enzyme) which is indicative of detoxification events.

Accordingly, in one embodiment, the present invention provides a formulation for improving liver health that includes wasabi root fiber powder, artichoke leaf extract, asparagus extract, kudzu root extract, oregano extract, schisandra berry extract, notoginseng (ethanol extract of *Panax notoginseng* root), sanchi (water extracts from *Panax notoginseng* root), Gegen (*Pueraria omeiensis*), spinach dehydrate, or combinations thereof.

In another embodiment, the present invention provides a method of protecting the liver from carbon te[r]trachloride ("$CCl_4$") insults by providing wasabi root fiber powder, artichoke leaf extract, asparagus extract, kudzu root extract, oregano extract, schisandra berry extract, notoginseng (ethanol extract of *Panax notoginseng* root), sanchi (water extracts from *Panax notoginseng* root), Gegen (*Pueraria omeiensis*), spinach dehydrate, or combinations thereof.

In yet another embodiment, the present invention provides methods of protecting the liver from alcohol insults by providing wasabi root fiber powder, artichoke leaf extract, asparagus extract, kudzu root extract, oregano extract, schisandra berry extract, notoginseng (ethanol extract of *Panax notoginseng* root), sanchi (water extracts from *Panax notoginseng* root), Gegen (*Pueraria omeiensis*), spinach dehydrate, or combinations thereof.

In yet another embodiment, the present invention provides methods of inducing phase II enzymes by providing wasabi root fiber powder, artichoke leaf extract, asparagus extract, kudzu root extract, oregano extract, schisandra berry extract, notoginseng (ethanol extract of *Panax notoginseng* root), sanchi (water extracts from *Panax notoginseng* root), Gegen (*Pueraria omeiensis*), spinach dehydrate, or combinations thereof.

DETAILED DESCRIPTION OF THE INVENTION

Figure 1:
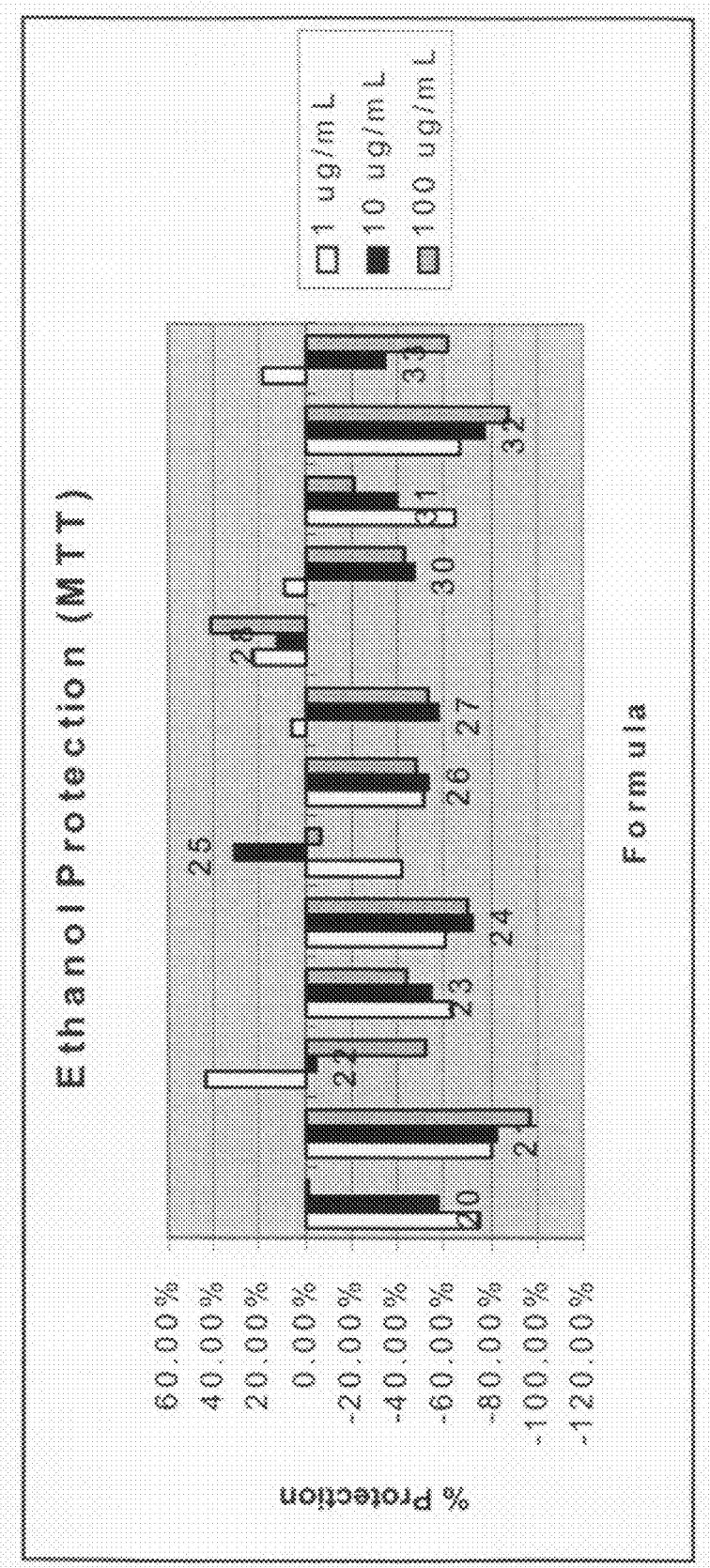
FIG. 1 is a bar graph showing the effect of various formulations in protecting the liver from ethanol insults as measured by MTT.

It is to be understood that this invention is not limited to the particular methodology or protocols described herein. Further, unless defined otherwise, all technical and scientific terms used herein have the same meaning as commonly understood to one of ordinary skill in the art to which this invention belongs. It is also to be understood that the terminology used herein is for the purpose of describing particular embodiments only, and is not intended to limit the scope of the present invention, which will be limited only by the claims.

Ingredients for Use in Formulations of the Present Invention

The present invention is based on the surprising discovery that unique combinations of the following ingredients, described more fully in Table 1, improve liver health: wasabi root fiber powder, artichoke leaf extract, asparagus extract, kudzu root extract, oregano extract, schisandra berry extract, notoginseng (ethanol extract of *Panax notoginseng* root), sanchi (water extracts from *Panax notoginseng* root), Gegen (*Pueraria omeiensis*), and spinach dehydrate.

TABLE 1

| Ingredient | Description |
| --- | --- |
| Artichoke leaf extract (*Cynara scolymus L.*) | Extracts from artichoke have been used in folk medicine against liver complaints and such extracts have been claimed to exert hepatotprotective effect. Journal of Ethno-pharmacology, 86, 203-211 (2003). Constituents include flavanoids and sesquiterpenoid bitter compounds of the |

TABLE 1-continued

| Ingredient | Description |
|---|---|
| | guaianolide-type. Czygan, Franz-Christian et al., Herbal Drugs and Phytopharmaceuticals, 3rd ed., Stuttgart, Germany, Medpharm Scientific Publishers, 2004. p. 174. Artichoke leaf extract can be obtained from Grupo Centroflora; Sao Paulo, Brazil. |
| *Asparagus* dehydrate | *Asparagus racemosus* (commonly known as Shatavari) is recommended in Ayurvedic texts for prevention and treatment of gastric ulcers, dyspepsia and as a galactogogue. *A. racemosus* has also been used successfully by some Ayurvedic practitioners for nervous disorders, inflammation, liver diseases and certain infectious diseases. However, no scientific proof justifying aforementioned uses of root extract of *A. racemosus* is available so far. Indian J Med Sci., 57(9): 408-14 (2003). Animal studies have also demonstrated beneficial antioxidant effects to the liver. Journal of Ethnopharmacology, 71, 425-435 (2003). The chemical constituents so far reported include flavonoids, oligosaccharides, amino acids, sulphur-contianing acids, and steroidal saponins. Id. |
| Kudzu root extract (*Pueraria lobata*) | Kudzu or *Pueraria Radix* is the root of *Pueraria lobata* which is a perennial leguminous vine native to eastern Asia. The active principles of *Pueraria lobata* are coumarins, isoflavonoids (puerarin, daidzin and daidzein), and sapoinins (soyasaponins, kudzusaponins). Kudzu has been used for many disorders such as fevers, gastrointerstinal disorders, muscle aches, allergies, respiratory problems, skin problems, high blood pressure, migraine headaches, lowering cholesterol, and treating chronic alcoholism. Clinical Chimica Acta, 347, 121-128 (2004). |
| Notoginseng (*Panax notoginseng*) | Notoginseng as referred to herein is the ethanol extract from *Panax notoginseng* root. The active constituents of *Panax notoginseng* include saponins (primarily ginsenosides), dencichines, flavonoids, and polysaccharide; however, the levels of these components vary in different geographical regions of growth and also show a seasonal variation. Dong, TT et al., Chemical assessment of roots of *Panax notoginseng* in China: regional and seasonal variations in its active constituents. J. Agric Food Chem, 51(16): 4617-23 (2003). *Panax notoginseng* is used to treat coronary heart disease, cardiac angina, and apoplexy. Notoginseng can be obtained from EUL International Herb Manufacturing, La Verne, California. |
| Gegen root extract (*Pueraria omeiensis*) | Commonly known as Omei Mountain Kudzu Vine. |
| Oregano extract | The constituents of oregano include two phenoles carvacrol and thymol (see also thyme and savory.) A variety of monoterpene hydrocarbons (limonene, terpinene, ocimene, caryophyllene, beta-bisabolene and p-cymene) and monoterpene alcohols (linalool, 4-terpineol) have also been found. |
| Sanchi (*Panax notoginseng*) | Sanchi is referred to herein as the water extract from *Panax notoginseng* root. *Panax notoginseng* is known to contain saponins. Sanchi can be obtained from Draco Natural Products, San Jose, California. |
| *Schisandra* berry extract (*Fructus schisandrae*) | *Schisandra* berry or *schizandra* berry is commonly known as Chinese Magnoliavine fruit. It is generally used to arrest discharges, promote fluid secretion, tonify the kidney, and induce sedation. See U.S. Pat. No. 6,455,078. *Schisandra* lignans have been cited to protect the liver against $CCl_4$ damage. Planta Medica, 61 (2); 134-7 (1995). |
| Spinach dehydrate | Spinach contains betaine which has been used clinically for liver disease. See US2003/0091615. Spinach dehydrate can be obtained from Access Business Group LLC, Ada, Michigan. |
| Wasabi root | Studies suggest that wasabi (*Wasabia japonica*, syn. *Eutrema* Wasabi) may generate an increase in the abundance of the protective phase II detoxification enzymes, such as glutathione S-transferase (GST), resulting in hepatoprotection. Recent identification of 6-methylsulfinylhexyl isothiocyanate (6-HITC), an analogue of sulforaphane (4-methylsulfinylbutyl isothiocyanate) isolated from broccoli, has been suggested to be the major GST inducer in wasabi. J. Biol Chem., 1; 277(5): 3456-63 (2002). It is known that wasabi contains isothiocyanate components. Id. Wasabi root extract can be obtained from EUL International Herb Manufacturing, La Verne, California. |

More specifically, the formulations of the present invention improve liver health by protecting the liver against alcohol and carbon tetrachloride insults. Additionally, the formulations improve liver health by inducing phase II enzymes. Phase II enzymes are responsible for removing potential carcinogens by aiding in their removal from the body.

"Protecting the liver against alcohol insults" and "protecting the liver against carbon tetrachloride insults" refers to the ability of a formulation described herein to preserve or improve existing liver function.

Formulations of the Present Invention

Table 2 illustrates representative daily amounts of the ingredients that can be included in the supplement.

TABLE 2

| Ingredient | Daily Dosage |
|---|---|
| Artichoke leaf extract | 200 mg-1000 mg |
| *Asparagus* extract | 100 mg-500 mg |
| Gegen root extract | 150 mg-1000 mg |
| Kudzu root extract | 150 mg-1000 mg |
| Notoginseng | 100 mg-500 mg |
| Oregano extract | 20 mg-500 mg |
| Sanchi | 100 mg-500 mg |
| *Schisandra* berry extract | 150 mg-1000 mg |
| Spinach dehydrate | 20 mg-500 mg |
| Wasabi root powder | 150 mg-500 mg |

EXAMPLES

The following are illustrative examples of formulations made into tablets according to this invention and it should be understood that they do not limit the scope of the invention.

Example 1

| Per: 3 Tablets Qty. | U/M | Item # | Ingredients | % W/W |
|---|---|---|---|---|
| 350.0 | mg | R7462 | Sanchi root concentrate | 18.88% |
| 300.00 | mg | R6911 | *Asparagus* dehydrate | 16.18% |
| 150.00 | mg | R7464 | Gegen root extract, 10% | 8.09% |
| 500.00 | mg | R7461 | Artichoke leaf extract, 5% | 26.97% |
| 150.00 | mg | NF9824Z | Spinach dehydrate | 8.09% |
| 310.0 | mg | R4174Q | Microcrystalline Cellulose, Silicified | 16.72% |

-continued

| Per: 3 Tablets Qty. | U/M | Item # | Ingredients | % W/W |
|---|---|---|---|---|
| 44.0 | mg | R3338 | Cellulose Gum | 2.37% |
| 5.6 | mg | R0225 | Silicon Dioxide, Fine Powder | 0.30% |
| 44.0 | Mg | R3512 | Stearic Acid, Powder, Vegetable | 2.37% |
| 11.0 | mg | NF6004 | Hydroxypropyl Methylcellulose | |

Example 2

| Per: 3 Tablets Qty. | U/M | Item # | Ingredients | % W/W |
|---|---|---|---|---|
| 500.0 | mg | R7461 | Artichoke powder extract | 30.10% |
| 150.00 | mg | R7460 | Wasabi root concentrate | 9.03% |
| 500.00 | mg | R7464 | Kudzu root, 40% | 30.10% |
| 150.00 | mg | R6910 | Oregano Extract | 9.03% |
| 278.0 | mg | R4174Q | Microcrystalline Cellulose, Silicified | 16.74% |
| 39.0 | mg | R3338 | Cellulose Gum | 2.35% |
| 5.0 | mg | R0225 | Silicon Dioxide, Fine Powder | 0.30% |
| 39.0 | mg | R3512 | Stearic Acid, Powder, Vegetable | 2.35% |
| 11.0 | mg | HPMC | Hydroxypropyl Methylcellulose | |

Example 3

| Per: 3 Tablets Qty. | U/M | Item # | Ingredients | % W/W |
|---|---|---|---|---|
| 150.00 | mg | R7462 | Sanchi | 8.15% |
| 150.00 | mg | R7521 | Notoginseng | 8.15% |
| 500.00 | mg | R7461 | Artichoke leaf extract, 5% | 27.18% |
| 500.00 | mg | R7463 | Kudzu root extract | 27.18% |
| 150.00 | mg | R6910 | Oregano Extract | 8.15% |
| 300.0 | mg | R4174Q | Microcrystalline Cellulose, Silicified | 16.31% |
| 42.0 | mg | R3338 | Cellulose Gum, Modified NF | 2.28% |
| 5.5 | mg | R0225 | Silicon Dioxide, NF Fine Powder | 0.30% |
| 42.0 | mg | R3512 | Stearic Acid, Powder, Vegetable | 2.28% |
| 13.0 | mg | NF6004 | Hydroxypropyl Methylcellulose | |

Example 4

| Per: 3 Tablets Qty. | U/M | Item # | Ingredients | % W/W |
|---|---|---|---|---|
| 350.0 | mg | R7462 | Sanchi | 20.42% |
| 300.00 | mg | R6911 | *Asparagus* dehydrate | 17.50% |
| 500.00 | mg | R7461 | Artichoke leaf extract, 5% | 29.17% |
| 200.00 | mg | NF9824Z | Spinach dehydrate | 11.67% |
| 280.0 | mg | R4174Q | Microcrystalline Cellulose, Silicified | 16.34% |
| 39.0 | mg | R3338 | Cellulose Gum | 2.28% |
| 5.0 | mg | R0225 | Silicon Dioxide, Fine Powder | 0.29% |
| 40.0 | mg | R3512 | Stearic Acid, Powder, Vegetable | 2.33% |
| 12.0 | mg | NF6004 | Hydroxypropyl Methylcellulose | |

Example 5

| Per: 3 Tablets Qty. | U/M | Item # | Ingredients | % W/W |
|---|---|---|---|---|
| 500.00 | mg | R7461 | Artichoke leaf extract | 27.18% |
| 500.00 | mg | R7463 | Kudzu root extract, 40% | 27.18% |
| 150.00 | mg | R7521 | Notoginseng | 8.15% |
| 150.00 | mg | R7460 | Wasabi fiber powder | 8.15% |
| 150.00 | mg | NF9824Z | Spinach dehydrate | 8.15% |
| 300.0 | mg | R4174Q | Microcrystalline Cellulose, Silicified | 16.31% |
| 42.0 | mg | R3338 | Cellulose Gum | 2.28% |
| 5.6 | mg | R0225 | Silicon Dioxide, Fine Powder | 0.30% |
| 42.0 | mg | R3512 | Stearic Acid, Powder, Vegetable | 2.28% |
| 11.0 | mg | NF6004 | Hydroxypropyl Methylcellulose | |

Example 6

| Per 3 Tablets Qty. | U/M | Item # | Ingredients | % W/W |
|---|---|---|---|---|
| 500.0 | mg | R7461 | Artichoke leaf extract, 5% | 23.88% |
| 500.00 | mg | R7460 | Wasabi fiber Powder | 23.88% |
| 500.00 | mg | R7464 | Gegen Root extract, 10% | 23.88% |
| 150.00 | mg | R6910 | Oregano Extract | 7.16% |
| 342.0 | mg | R4174Q | Microcrystalline Cellulose, Silicified | 16.33% |
| 48.0 | mg | R3338 | Cellulose Gum | 2.29% |
| 6.2 | mg | R0225 | Silicon Dioxide, Fine Powder | 0.30% |
| 48.0 | mg | R3512 | Stearic Acid, Powder, Vegetable | 2.29% |
| 11.0 | mg | NF6004 | Hydroxypropyl Methylcellulose | |

Example 7

| Per 2 Tablets Qty. | U/M | Item # | Ingredients | % W/W |
|---|---|---|---|---|
| 150.0 | mg | R7460 | Wasabi root fiber powder | 8.83% |
| 500.00 | mg | R7461 | Artichoke leaf extract, 5% | 29.43% |
| 300.00 | mg | R3490 | *Schizandra* berry ext | 17.66% |
| 150.00 | mg | R7521 | Notoginseng | 8.83% |
| 150.00 | mg | NF9824Z | Spinach dehydrate | 8.83% |
| 346.0 | mg | R4174Q | Microcrystalline Cellulose, Silicified | 20.36% |
| 49.0 | mg | R3338 | Cellulose Gum | 2.88% |
| 5.1 | mg | R0225 | Silicon Dioxide, Fine Powder | 0.30% |
| 49.0 | mg | R3512 | Stearic Acid, Powder, Vegetable | 2.88% |
| 11.0 | mg | NF6004 | Hydroxypropyl Methylcellulose | |

Example 8

| Per 3 Tablets Qty. | U/M | Item # | Ingredients | % W/W |
|---|---|---|---|---|
| 150.0 | mg | R7460 | Wasabi root fiber powder | 7.62% |
| 500.00 | mg | R7461 | Artichoke leaf extract, 5% | 25.41% |
| 500.00 | mg | R7463 | Kudzu root, 40% | 25.41% |
| 150.00 | mg | R7521 | Notoginseng | 7.62% |

-continued

| Per 3 Tablets Qty. | U/M | Item # | Ingredients | % W/W |
|---|---|---|---|---|
| 150.00 | mg | R6910 | Oregano extract | 7.62% |
| 400.0 | mg | R4174Q | Microcrystalline Cellulose, Silicified | 20.33% |
| 55.0 | mg | R3338 | Cellulose Gum | 2.79% |
| 5.9 | mg | R0225 | Silicon Dioxide, Fine Powder | 0.30% |
| 38.0 | mg | R3512 | Stearic Acid, Powder, Vegetable | 2.90% |
| 11.0 | mg | NF6004 | HPMC | |

Example 9

| Label Per: 2 Tablets Qty. | U/M | Item # | Ingredients | % W/W |
|---|---|---|---|---|
| 500.00 | Mg | R7461 | Artichoke leaf extract, 5% | 32.16% |
| 500.00 | Mg | R7463 | Kudzu root extract, 40% | 32.16% |
| 150.00 | Mg | R6910 | Oregano Extract | 9.65% |
| 315.0 | mg | R4174Q | Microcrystalline Cellulose, Silicified | 20.26% |
| 40.0 | Mg | R3338 | Cellulose Gum, Modified NF | 2.57% |
| 4.7 | mg | R0225 | Silicon Dioxide, NF Fine Powder | 0.30% |
| 45.0 | mg | R3512 | Stearic Acid, Powder, Vegetable | 2.89% |
| 11.0 | mg | NF6004 | HPMC | |

The above exemplary tabletted formulations can be manufactured according to typical methods known in the industry. For example, wasabi root fiber powder, artichoke leaf extract, schizandra berry extract, notoginseng and spinach dehydrate are passed through a SWECO separator equipped with a 20 mesh screen into a 100 cubic foot PK blender. Microcrystalline cellulose is added to the blend in the PK blender. The ingredients are blended for ten minutes. Cellulose gum and silicon dioxide are passed through a SWECO separator equipped with a 20 mesh screen directly into the 100 cubic foot PK blender. The ingredients are blended for ten minutes. Next, stearic acid is passed through a SWECO separator equipped with a 20 mesh screen directly into the 100 cubic foot PK blender. The mixture is blended for an additional five minutes. The resulting mixture is discharged into totes or supersacks, and compressed into tablets.

Methods of Administration

Formulations of the present invention may be formulated in an acceptable carrier and may be prepared, packaged, and labeled for promoting health, liver function, protecting against alcohol and/or chemical insults to the liver, and/or inducing phase II enzymes to promote healthy liver function. The formulations of the present invention and their acceptable carriers may be formulated for oral administration in the form of a pill, tablet, dried or powdered product for reconstitution with water or other suitable vehicle before use, bar, food, solution, syrup, suspension, beverage, lozenge, etc. The formulations of the present invention may also be parenterally administered or administered by inhalation or insufflation (either through the mouth or nose).

Liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). When administered in the form of a beverage, formulations of the present invention may be water-based, milk-based, tea-based, fruit juice-based, or some combination thereof.

Formulations of the present invention may also be orally administered in the form of a solid prepared by conventional means with pharmaceutically acceptable excipients such as binding agents (e.g., pregelatinized maize starch, polyvinyl pyrrolidone or hydroxypropyl methylcellulose ("HPMC")); fillers (e.g., lactose, microcrystalline cellulose or calcium hydrogen phosphate); lubricants (e.g., magnesium stearate, talc or silica); disintegrants (e.g., cellulose gum, potato starch or sodium starch glycolate); or wetting agents (e.g., sodium lauryl sulphate).

Formulations of the present invention that are orally administered can further comprise thickeners, including xanthum gum, carbosymethyl-cellulose, carboxyethylcellulose, hydroxyporpolcellulose, methylcellulose, microcrystalline cellulose, starches, dextrins, fermented whey, tofu, maltodextrins, polyols, including sugar alcohols (e.g., sorbitol and mannitol), carbohydrates (e.g. lactose), propylene glycol alginate, gellan gum, guar, pectin, tragacanth gum, gum acacia, locust bean gum, gum arabic, gelatin, as well as mixtures of these thickeners.

Orally administered formulations of the present invention can contain an effective amount of one or more sweeteners, including carbohydrate sweeteners and natural and/or artificial no/low calorie sweeteners. The amount of the sweetener used in the formulations of the present invention will vary, but typically depends on the type of sweetener used and the sweetness intensity desired.

In addition to the formulations described previously, the compounds may also be a formulated as a sustained and/or timed release formulation. The formulations must be maintained above some minimum therapeutic dose to be effective. Common timed and/or controlled release delivery systems include, but are not be restricted to, starches, osmotic pumps, or gelatin micro capsules.

The formulations may, if desired, be presented in a pack or dispenser device which may comprise one or more unit dosage forms comprising a formulation of the present invention. The pack may for example comprise metal or plastic foil, such as a blister pack. The pack or dispenser device may be accompanied by instructions for administration.

Other useful dosage forms can be prepared by methods and techniques that will be well understood by those of skill in the art and may include the use of additional ingredients in producing tablets, capsules, or liquid dosage forms. The dose, and dose frequency, will vary according to the age, body weight, condition and response of the individual consumer or patient, and the particular formulation of the present invention that is used.

It is intended that the foregoing detailed description be regarded as illustrative rather than limiting. The present invention is further illustrated by the following experimental investigations and examples, which should not be construed as limiting.

Bioassay Study on Individual Ingredients

Several materials were submitted for bioassay testing to try to predict their protective ability against alcohol and chemically induced liver damage. To assess this, human liver cells were treated with the material and an insult, and cell viability was measured using two different assays. Alcohol damage was mimicked using 2.5% ethanol as the insult. $CCl_4$ at 0.2% was used for the chemical insult. These concentrations were chosen because they were the concentrations that produced 20% cell death in preliminary experiments, and would therefore not cause the cells to undergo irreversible cell death/damage.

Materials were tested at three concentrations (1, 10 and 100 μg/mL) and an estimation of the EC-50 was determined (see Experimental section below for more details). In addition to the cell viability assays, Phase II Enzyme Induction testing was also conducted to determine if a material had detoxification properties. The Phase II Enzyme Induction assay measures a sample's ability to induce quinone reductase (a Phase II enzyme) which is indicative of detoxification events. Phase II enzymes are responsible for removing potential carcinogens by aiding in their removal from the body. Broccoli is known as a good Phase II enzyme inducer because of its sulforaphane content. Pure sulforaphane has activity at $10^6$ U/g, while broccoli has reported activity from 4000-74,000 U/g (dependent on variety, form, and/or extraction conditions). Activity above 30,000 U/g is considered excellent. Activity less than 5000 U/g is considered minimal. Most materials that are considered good Phase II Enzyme inducers will have activity between 15,000-30,000 U/g.

Tables 3 and 4 summarize the EC-50 values of all materials tested. Table 3 is specifically for results of the ethanol protection, and Table 4 for carbon tetrachloride. Table 5 gives the results of the Phase II Enzyme Induction assay.

TABLE 3

EC-50 results of the MTT and LDH assays for Ethanol protection assessment.

| Sample | Description | EC-50 MTT (μg/mL) | EC-50 LDH (μg/mL) |
|---|---|---|---|
| CD-2808 | *Hibiscus* SD Powder | 10-100 | None |
| CD-4230 | Picao Pret (*Bidens Pilosa*) Herb | None | >100 |
| CD-4228 | *Pueraria* (Kudzu) Root 40% | <1 | None |
| CD-3902 | Cardoon SD Powder | >100 | None |
| CD-4229 | Gegen root extract (*pueraria omeiensis*), 10% | None | None |
| CD-4796 | Beet Powder | 100 | >100 |
| CD-4775 | *Aframomum* S/D Powder | None | >100 |
| CD-4788 | *Schisandra* berry Extract | None | >100 |
| CD-4780 | *Asparagus* Dehydrate | None | None |
| CD-4793 | *Bidens Pilosa* Extract | None | None |
| CD-4787 | *Picrorhiza Kurrooa* Extract | None | >100 |
| CD-4786 | *Eclipta Alba* Extract | None | None |
| CD-4795 | Curcumin 95% | None | None |
| CD-4792 | Boldo Extract | None | >100 |
| CD-5347 | Szechuan Lovage Rhizome | <1 | >100 |
| CD-5345 | Sanchi | <1 | >100 |
| CD-5346 | *Glycyrrhiza Uralensis* Fisch Root | <1 | >100 |
| CD-5348 | Artichoke Extract Powder, 5% Cynarin | <1 | >100 |
| CD-5349 | Artichoke Extract Powder, 2.5% Cynarin | <1 | >100 |
| CD-5350 | Chanca Piedra Extract 3:1 | <1 | >100 |
| CD-5383 | Kudzu Extract Powder 40% | None | None |
| CD-5384 | Tree Peony Bark 1:8 | None | None |
| CD-5385 | Gegen Extract | None | None |
| CD-5386 | *Pueraria* 40% | <1 | >100 |
| CD-5442 | *Curcuma Longa* Extract 10:1 | None | None |
| CD-5441 | Moutan Extract 12:1 | None | None |
| CD-5440 | Notoginseng Extract 10% | None | 10-100 |
| CD-5548 | Silybin Complex | None | None |
| CD-5550 | Dandelion 4:1 | None | None |
| CD-5549 | Milk Thistle 70% Granular | None | None |
| CD-5624 | Oregano S/D Powder | None | None |
| CD-5728 | Holy Basil S/D Powder | None | None |
| CD5730 | Holy Basil S/D Powder | None | None |
| CD-5741 | Sage S/D Powder | None | None |
| CD-5241 | Gegen Extract 10% | None | 10-100 |
| CD-5796 | Radix Notoginseng | None | 10-100 |
| CD-5797 | Artichoke Extract Powder 5% | 1 | >100 |
| CD-5798 | Rhizoma *Curcumae Longae* | None | None |
| CD-5799 | Rhizoma Chuanxiong | None | >100 |
| CD-5800 | Semen *Armeniacae Amarum* | None | >100 |
| CD-5801 | Tree Bark Extract 8:1 | None | >100 |
| CD-5802 | Cortex Moutan | None | None |
| CD-5803 | Radix *Glycyrrhizae* | >100 | >100 |
| CD-5707 | *Wasibia Japonica* Powder 100% | None | >100 |
| CD-5863 | Wasabi Root P.E. 5:1 | >100 | 100 |
| CD-5864 | Wasabi Earhnut P.E. 5:1 | 10-100 | 10-100 |
| CD-5865 | Wasabi Fibre P.E. 5:1 | 10-100 | >100 |
| CD-5866 | Wasabi Root Powder | >100 | >100 |
| CD-5867 | Wasabi Earthnut Powder | >100 | >100 |
| CD-5868 | Wasabi Fibre Powder | >100 | >100 |

TABLE 4

EC-50 results of the MTT and LDH assays for CCl4 protection assessment.

| Sample | Description | EC-50 MTT (μg/mL) | EC-50 LDH (μg/mL) |
|---|---|---|---|
| CD-2808 | *Hibiscus* SD Powder | None | 1 |
| CD-4230 | Picao Pret (*Bidens Pilosa*) Herb | 1-10 | None |
| CD-4228 | *Pueraria* (Kudzu) Root 40% | 1-10 | None |
| CD-3902 | Cardoon SD Powder | None | <1 |
| CD-4229 | Gegen (Kudzu Root) 10% | None | <1 |
| CD-4796 | Beet Powder | None | 1 |
| CD-4775 | *Aframomum* S/D Powder | None | <1 |
| CD-4788 | *Schisandra* Berry Extract | None | 1-10 |
| CD-4780 | *Asparagus* Dehydrate | None | <1 |
| CD-4793 | *Bidens Pilosa* Extract | None | <1 |
| CD-4787 | *Picrorhiza Kurrooa* Extract | 100 | 1 |
| CD-4786 | *Eclipta Alba* Extract | >100 | <1 |
| CD-4795 | Curcumin 95% | None | <1 |
| CD-4792 | Boldo Extract | None | <1 |
| CD-5347 | Szechuan Lovage Rhizome | >100 | None |
| CD-5345 | Sanchi | 10-100 | 1-10 |
| CD-5346 | *Glycyrrhiza Uralensis* Fisch Root | >100 | 1-10 |
| CD-5348 | Artichoke Extract Powder, 5% Cynarin. | 100 | <1 |
| CD-5349 | Artichoke Extract Powder, 2.5% Cynarin | >100 | None |
| CD-5350 | Chanca Piedra Extract 3:1 | >100 | 100 |
| CD-5383 | Kudzu Extract Powder 40% | 10-100 | 100 |
| CD-5384 | Tree Peony Bark 1:8 | 10-100 | 1-10 |
| CD-5385 | Gegen Extract | 10-100 | <1 |
| CD-5442 | *Curcuma Longa* Extract 10:1 | <1 | 1-10 |
| CD-5441 | Moutan Extract 12:1 | 1-10 | 1-10 |
| CD-5440 | Notoginseng Extract 10% | <1 | <1 |
| CD-5548 | Silybin Complex | None | None |
| CD-5550 | Dandelion 4:1 | 10-100 | >100 |
| CD-5549 | Milk Thistle 70% Granular | None | >100 |
| CD-5624 | Oregano S/D Powder | None | >100 |
| CD-5728 | Holy Basil S/D Powder | None | >100 |
| CD5730 | Holy Basil S/D Powder | None | None |
| CD-5741 | Sage S/D Powder | None | None |
| CD-5241 | Gegen Extract 10% | 10-100 | 1-10 |
| CD-5796 | Radix Notoginseng | 1-10 | >100 |
| CD-5797 | Artichoke Extract Powder 5% | 1-10 | 1-10 |
| CD-5798 | Rhizoma *Curcumae Longae* | None | 1-10 |
| CD-5799 | Rhizoma Chuanxiong | None | >100 |

TABLE 4-continued

EC-50 results of the MTT and LDH assays for CCl4 protection assessment.

| Sample | Description | EC-50 MTT (µg/mL) | EC-50 LDH (µg/mL) |
|---|---|---|---|
| CD-5800 | Semen *Armeniacae Amarum* | None | None |
| CD-5801 | Tree Bark Extract 8:1 | >100 | >100 |
| CD-5802 | Cortex Moutan | 10-100 | None |
| CD-5803 | Radix *Glycyrrhizae* | 10-100 | None |
| CD-5707 | *Wasibia Japonica* Powder 100% | >100 | >100 |
| CD-5863 | Wasabi Root P.E. 5:1 | >100 | 1-10 |
| CD-5864 | Wasabi Earhnut P.E. 5:1 | 10-100 | 10-100 |
| CD-5865 | Wasabi Fibre P.E. 5:1 | 10 | 1-10 |
| CD-5866 | Wasabi Root Powder | None | 1-10 |
| CD-5867 | Wasabi Earthnut Powder | 1-10 | 10-100 |
| CD-5868 | Wasabi Fibre Powder | 10-100 | 10-100 |

TABLE 5

Phase II Enzyme (Quinone Reductase) Induction Assay Results

| Sample | Description | U/g | Rank |
|---|---|---|---|
| CD-2808 | *Hibiscus* SD Powder | 14,493 | ++ |
| CD-4230 | Picao Pret (*Bidens Pilosa*) Herb | 24,691 | ++ |
| CD-4228 | Kudzu Root 40% | 25,641 | ++ |
| CD-3902 | Cardoon SD Powder | Not Tested | Not Tested |
| CD-4229 | Gegen (Kudzu Root) 10% | 95,238 | ++++ |
| CD-4796 | Beet Powder | 9132 | ++ |
| CD-4775 | *Aframomum* S/D Powder | Not Tested | Not Tested |
| CD-4788 | *Schisandra* Berry Extract | 30,303 | ++++ |
| CD-4780 | *Asparagus* Dehydrate | Not Tested | Not Tested |
| CD-4793 | *Bidens Pilosa* Extract | 9132 | ++ |
| CD-4787 | *Picrorhiza Kurrooa* Extract | 5420 | ++ |
| CD-4786 | *Eclipta Alba* Extract | 10,101 | ++ |
| CD-4795 | Curcumin 95% | NR** | NR** |
| CD-4792 | Boldo Extract | 13,605 | ++ |
| CD-5347 | Szechuan Lovage Rhizome | 11,299 | ++ |
| CD-5345 | Sanchi | 13,333 | ++ |
| CD-5346 | *Glycyrrhiza Uralensis* Fisch Root | 14,815 | ++ |
| CD-5348 | Artichoke Extract Powder, 5% Cynarin | 27,778 | +++ |
| CD-5349 | Artichoke Extract Powder, 2.5% Cynarin | 44,444 | ++++ |
| CD-5350 | Chanca Piedra Extract 3:1 | 95,238 | ++++ |
| CD-5383 | Kudzu Extract Powder 40% | 55,556 | ++++ |
| CD-5384 | Tree Peony Bark 1:8 | 15,504 | ++ |
| CD-5385 | Gegen Extract | 95,238 | ++++ |
| CD-5442 | *Curcuma Longa* Extract 10:1 | NR* | NR* |
| CD-5441 | Moutan Extract 12:1 | 11,111 | ++ |
| CD-5440 | Notoginseng Extract 10% | 6006 | ++ |
| CD-5548 | Silybin Complex | NR** | NR** |
| CD-5550 | Dandelion 4:1 | NR** | NR** |
| CD-5549 | Milk Thistle 70% Granular | NR** | NR** |
| CD-5624 | Oregano S/D Powder | 95,238 | ++++ |
| CD-5728 | Holy Basil S/D Powder | 31,746 | ++++ |
| CD5730 | Holy Basil S/D Powder | 31,746 | ++++ |
| CD-5741 | Sage S/D Powder | 35,088 | ++++ |
| CD-5241 | Gegen Extract 10% | 37,037 | ++++ |
| CD-5796 | Radix Notoginseng | 15,504 | +++ |
| CD-5797 | Artichoke Extract Powder 5% | 9524 | ++ |
| CD-5798 | Rhizoma *Curcumae Longae* | 83,333 | ++++ |
| CD-5799 | Rhizoma *Chuanxiong* | 27,778 | +++ |
| CD-5800 | Semen *Armeniacae Amarum* | 22,222 | +++ |
| CD-5801 | Tree Bark Extract 8:1 | 17,544 | +++ |
| CD-5802 | Cortex Moutan | 21,505 | +++ |
| CD-5803 | Radix *Glycyrrhizae* | 11,494 | ++ |
| CD-5707 | *Wasibia Japonica* Powder 100% | 74,074 | ++++ |
| CD-5863 | Wasabi Root P.E. 5:1 | 10,753 | ++ |
| CD-5864 | Wasabi Earhnut P.E. 5:1 | 83,333 | ++++ |
| CD-5865 | Wasabi Fibre P.E. 5:1 | 12,346 | ++ |
| CD-5866 | Wasabi Root Powder | 30,303 | ++++ |
| CD-5867 | Wasabi Earthnut Powder | 5012 | ++ |
| CD-5868 | Wasabi Fibre Powder | 133,333 | ++++ |

*Inducer units per gram of fresh weight of material.
− = Negligible activity,
+ = Little activity,
++ = Good activity,
+++ = Very good activity,
++++ = Excellent activity.
**Not reportable due to toxicity to cells.

Experimental

For the ethanol protection and $CCl_4$ assessments, stock sample solutions are made in DMSO, then diluted in cell culture media for testing. Treatment of HepG2 cells (human liver cell line) is done by adding 100 µL of sample to each of three wells of a 96-well microtiter plate. After a 4 hour incubation, the insult is added (2.5% ethanol or 0.2% carbon tetrachloride) and an additional overnight incubation period is conducted. The next day, cell viability is measured using two different assays. First, using the CytoTox-ONE Homogenous Membrane Integrity Assay by Promega, the number of non-viable cells is estimated by measuring the release of lactate dehydrogenase (LDH) into the media. LDH leaks out of the cell when the cell membrane is compromised. The second assay is the MTT assay, which measures the reduction of a yellow tetrazolim salt (MTT) into an insoluble purple formazen product by the mitochondria of viable cells. Following an incubation with the MTT solution, isopropanol is added to solubilize the colored crystals. The amount of color produced is directly proportional to the number of viable cells.

For the phase II enzyme induction assay, stock sample solutions are made in acetonitrile, then diluted in cell culture media for testing. Treatment of Hepa1c1c7 cells (murine hepatoma cell line) is done by adding 150 µL of sample to each of three wells, in a 96-well microtiter plate. After 48 hours incubation, induction activity of quinone reductase is established by measuring the NADPH-dependent, menadiol-mediated reduction of MTT. Activity is reported as inducer units per gram of fresh weight of material, where one unit of inducer activity is defined as the amount of inducer required to double the quinone reductase specific activity of Hepa1c1c7 cells.

Bioassay Study on Ingredient Combinations

Several blends of liver detoxification ingredients were submitted for bioassay testing to try to predict their protective ability against alcohol and chemically induced liver damage. These blends were tested alongside two products already on the market for liver health—NUTRILITE® Milk Thistle and Dandelion and China's King Drink. To assess this, human liver cells were treated with the sample and an insult, and cell viability was measured using two different assays. Alcohol damage was mimicked using 2.5% ethanol as the insult. $CCl_4$ at 0.2% was used for the chemical insult. These concentrations were chosen because they were the concentrations that produced 20% cell death in preliminary experiments, and would therefore not cause the cells to undergo irreversible cell death/damage. Samples were tested at three concentrations (1, 10 and 100 µg/mL) and an estimation of the EC-50 was determined (see Experimental section below for more details). Materials with EC-50 values at or below 10 µg/mL are indicative of being the most efficacious, assuming 10% absorption of the material in 5 L of blood (average human volume).

Figure 2:
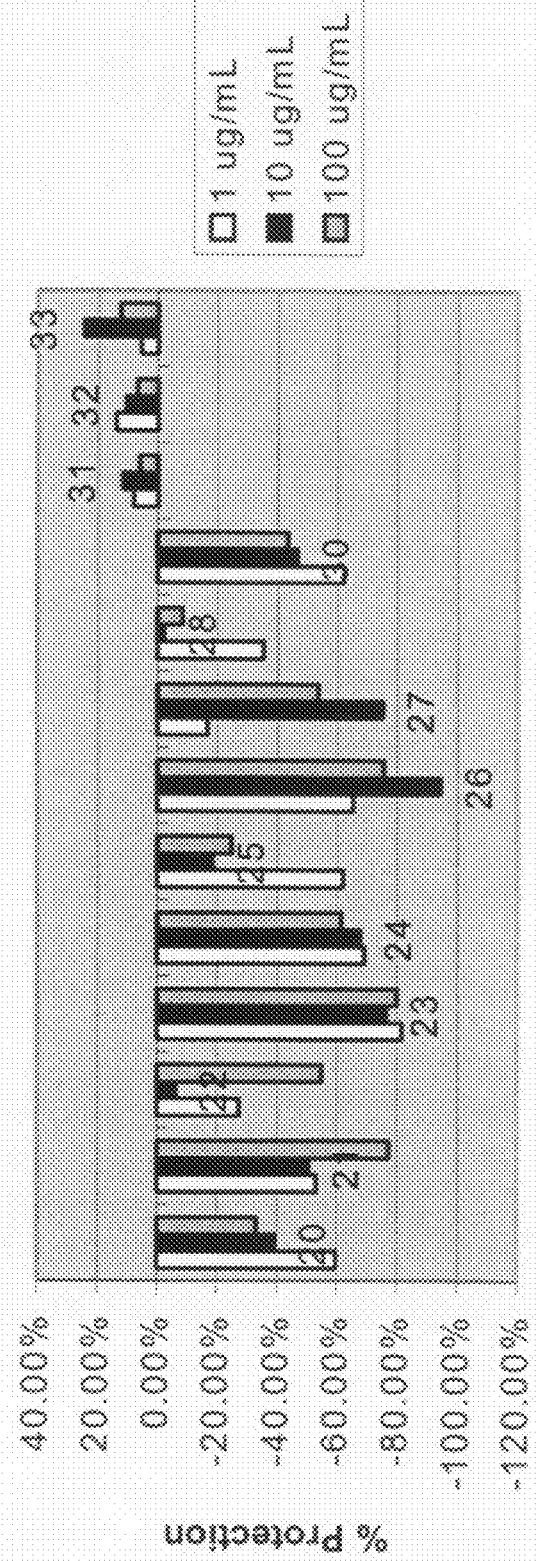
FIG. 2 is a bar graph showing the effect of various formulations in protecting the liver from ethanol insults as measured by LDH.
Figure 3:
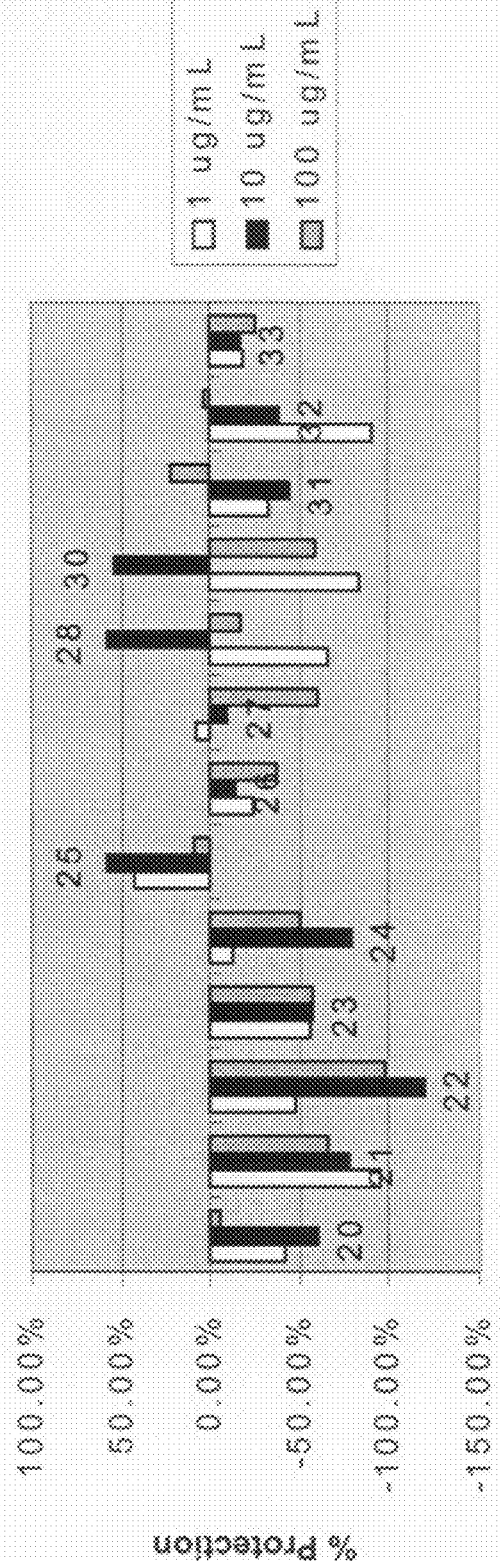
FIG. 3 is a bar graph showing the effect of various formulations in protecting the liver from $CCl_4$ insults as measured by MTT.
Figure 4:
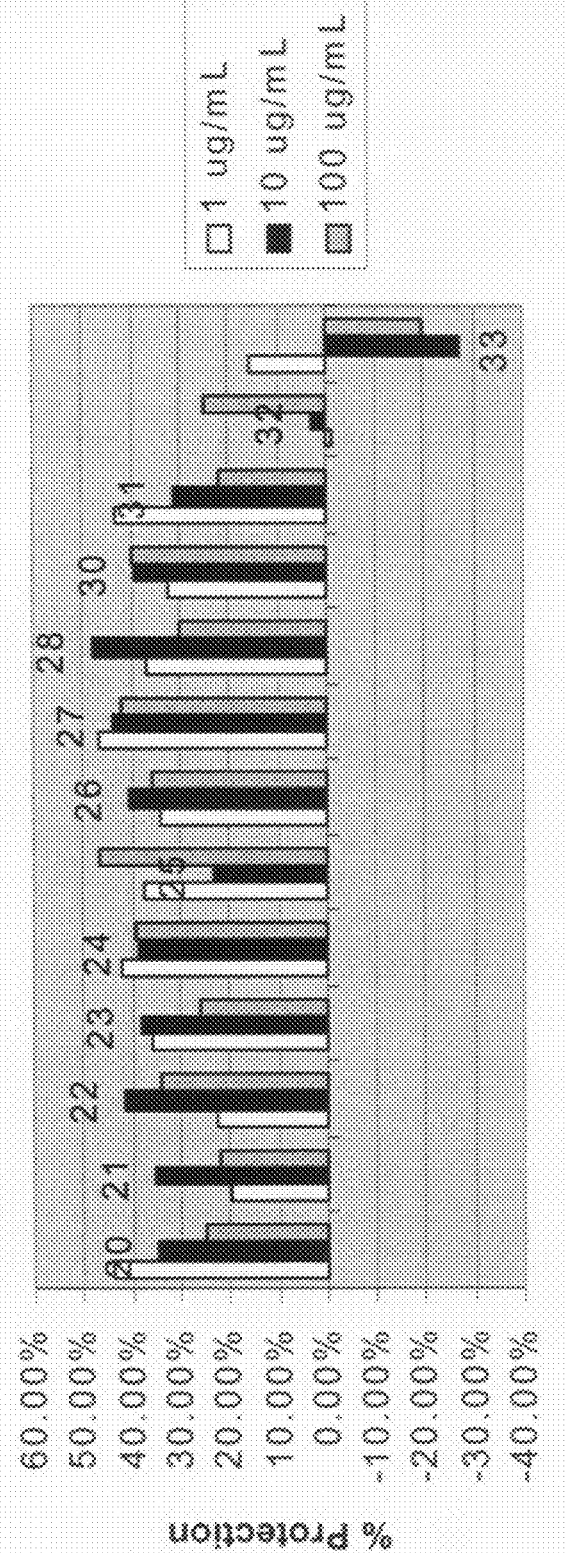
FIG. 4 is a bar graph showing the effect of various formulations in protecting the liver from $CCl_4$ insults as measured by LDH.

The blends that showed the greatest efficacy against $CCl_4$ liver cell damage were 8523-25-CI (Example 1), 8523-27-CI (Example 8), 8523-28-CI (Example 2), and 8523-30-CI (Example 3). Other blends that performed well (exhibited 40% protection at $\leqq 10$ µg/mL) were 8523-20-CI, 8523-22-CI, 8523-24-CI, 8523-26-CI and 8523-31-CI. None of the blends showed efficacy at $\leqq 10$ µg/mL against ethanol liver cell damage. The control products (NUTRILITE milk thistle and King Drink) also did not achieve EC-50 values of $\leqq 10$ µg/mL. The blends that had EC-50 values >100 µg/mL were 8523-28-CI (Example 2), 8523-30-CI (Example 3), 8523-31-CI (Example 4) and 8523-32-CI (Example 5). Tables 6-9 summarize the results of all the samples tested. These results are also seen in FIGS. 1-4.

TABLE 6

Results of the MTT assays for ethanol protection assessment

| Sample Number | Formula Number or Sample Name | 1 ug/mL | +/− | 10 ug/mL | +/− | 100 ug/mL | +/− | EC-50 |
|---|---|---|---|---|---|---|---|---|
| NF6523 | 8523-20-CI | −73% | 6% | −58% | 4% | −1% | 7% | — |
| NF6523 | 8523-21-CI | −80% | 5% | −82% | 3% | −97% | 11% | — |
| NF6523 | 8523-22-CI | 43% | 4% | −4% | 4% | −52% | 12% | * |
| NF6523 | 8523-23-CI | −63% | 2% | −55% | 4% | −44% | 3% | — |
| NF6523 | 8523-24-CI | −61% | 1% | −72% | 2% | −70% | 4% | — |
| NF6523 | 8523-25-CI | −42% | 4% | 31% | 3% | −7% | 1% | — |
| NF6523 | 8523-26-CI | −51% | 6% | −54% | 5% | −49% | 11% | — |
| NF6523 | 8523-27-CI | 6% | 6% | −58% | 4% | −53% | 6% | — |
| NF6523 | 8523-28-CI | 22% | 22% | 12% | 18% | 41% | 15% | >100 |
| NF6523 | 8523-30-CI | 9% | 25% | −48% | 17% | −43% | 16% | — |
| NF6523 | 8523-31-CI | −65% | 3% | −39% | 4% | −22% | 5% | — |
| NF6523 | 8523-32-CI | −67% | 8% | −77% | 8% | −88% | 5% | — |
| NF6523 | 8523-33-CI | 19% | 8% | −35% | 20% | −62% | 8% | — |
|  | Milk Thistle | −53% | 3% | −54% | 8% | −42% | 4 | — |
| CD5439 | King Drink | −57% | 3% | −13% | 17% | −8% | 6% | — |

(* = achieved EC-40 at one or more concentration)

TABLE 7

EC-50 results of the LDH assays for ethanol protection assessment.

| Sample Number | Formula Number or Sample Name | 1 ug/mL | +/− | 10 ug/mL | +/− | 100 ug/mL | +/− | EC-50 |
|---|---|---|---|---|---|---|---|---|
| NF6523 | 8523-20-CI | −60% | 20% | −39% | 12% | −33% | 5% | — |
| NF6523 | 8523-21-CI | −53% | 17% | −51% | 15% | −77% | 8% | — |
| NF6523 | 8523-22-CI | −27% | 4% | −6% | 16% | −55% | 11% | — |
| NF6523 | 8523-23-CI | −82% | 7% | −77% | 4% | −80% | 4% | — |
| NF6523 | 8523-24-CI | −69% | 2% | −68% | 9% | −61% | 5% | — |
| NF6523 | 8523-25-CI | −62% | 8% | −19% | 2% | −25% | 4% | — |
| NF6523 | 8523-26-CI | −65% | 7% | −94% | 7% | −76% | 1% | — |
| NF6523 | 8523-27-CI | −17% | 6% | −75% | 6% | −54% | 6% | — |
| NF6523 | 8523-28-CI | −35% | 15% | −2% | 5% | −8% | 13% | — |
| NF6523 | 8523-30-CI | −62% | 10% | −47% | 14% | −43% | 20% | — |
| NF6523 | 8523-31-CI | 8% | 18% | 12% | 5% | 6% | 23% | >100 |
| NF6523 | 8523-32-CI | 14% | 23% | 10% | 21% | 7% | 25% | >100 |
| NF6523 | 8523-33-CI | 5% | 2% | 25% | 1% | 13% | 24% | >100 |
|  | Milk Thistle | −23% | 2% | −24% | 6% | −7% | 7% | — |
| CD5439 | King Drink | −26% | 10% | 1% | 6% | 1% | 12% | >100 |

(* = achieved EC-40 at one or more concentration)

TABLE 8

EC-50 results of the MTT assays for CCl4 protection assessment.

| Sample Number | Formula Number or Sample Name | 1 ug/mL | +/− | 10 ug/mL | +/− | 100 ug/mL | +/− | EC-50 |
|---|---|---|---|---|---|---|---|---|
| NF6523 | 8523-20-CI | −42% | 10% | −60% | 11% | −6% | 17% | — |
| NF6523 | 8523-21-CI | −95% | 15% | −78% | 6% | −66% | 17% | — |
| NF6523 | 8523-22-CI | −47% | 22% | −120% | 21% | −97% | 3% | — |
| NF6523 | 8523-23-CI | −56% | 12% | −57% | 15% | −58% | 17% | — |
| NF6523 | 8523-24-CI | −12% | 12% | −80% | 18% | −50% | 14% | — |

TABLE 8-continued

EC-50 results of the MTT assays for CCl4 protection assessment.

| Sample Number | Formula Number or Sample Name | 1 ug/mL | +/− | 10 ug/mL | +/− | 100 ug/mL | +/− | EC-50 |
|---|---|---|---|---|---|---|---|---|
| NF6523 | 8523-25-CI | 42% | 1% | 58% | 2% | 9% | 29% | 1-10 |
| NF6523 | 8523-26-CI | −24% | 4% | −13% | 11% | −38% | 22% | — |
| NF6523 | 8523-27-CI | 8% | 13% | −9% | 15% | −61% | 5% | — |
| NF6523 | 8523-28-CI | −66% | 8% | 58% | 7% | −17% | 17% | 1-10 |
| NF6523 | 8523-30-CI | −84% | 19% | 54% | 11% | −59% | 23% | 1-10 |
| NF6523 | 8523-31-CI | −33% | 7% | −45% | 16% | 23% | 7% | >100 |
| NF6523 | 8523-32-CI | −91% | 10% | −39% | 5% | 4% | 16% | >100 |
| NF6523 | 8523-33-CI | −19% | 8% | −17% | 12% | −25% | 18% | — |
|  | Milk Thistle | −18% | 12% | −54% | 1% | −42% | 8% | — |
| CD5439 | King Drink | −67% | 13% | 33% | 6% | −22% | 13% | — |

(* = achieved EC-40 at one or more concentration)

TABLE 9

EC-50 results of the LDH assays for CCl4 protection assessment.

| Sample Number | Formula Number or Sample Name | 1 ug/mL | +/− | 10 ug/mL | +/− | 100 ug/mL | +/− | EC-50 |
|---|---|---|---|---|---|---|---|---|
| NF6523 | 8523-20-CI | 44% | 11% | 35% | 5% | 25% | 14% | * |
| NF6523 | 8523-21-CI | 20% | 20% | 35% | 11% | 22% | 15% | — |
| NF6523 | 8523-22-CI | 22% | 8% | 42% | 27% | 34% | 2% | * |
| NF6523 | 8523-23-CI | 36% | 13% | 38% | 5% | 26% | 6% | — |
| NF6523 | 8523-24-CI | 42% | 2% | 39% | 26% | 39% | 3% | * |
| NF6523 | 8523-25-CI | 38% | 9% | 23% | 1% | 47% | 11% | 100 |
| NF6523 | 8523-26-CI | 34% | 6% | 40% | 9% | 36% | 14% | * |
| NF6523 | 8523-27-CI | 47% | 0% | 44% | 0% | 42% | 9% | 1 |
| NF6523 | 8523-28-CI | 37% | 10% | 48% | 20% | 30% | 5% | 10 |
| NF6523 | 8523-30-CI | 32% | 6% | 39% | 2% | 40% | 4% | * |
| NF6523 | 8523-31-CI | 43% | 11% | 31% | 2% | 22% | 6% | * |
| NF6523 | 8523-32-CI | −1% | 27% | 3% | 28% | 25% | 26% | >100 |
| NF6523 | 8523-33-CI | 15% | 18% | −27% | 28% | −20% | 28% | — |
|  | Milk Thistle | 31% | 17% | 29% | 1% | 26% | 18% | >100 |
| CD5439 | King Drink | 30% | 13% | 32% | 6% | 50% | 19% | 100 |

(* = achieved EC-40 at one or more concentration)

In addition to the cell viability assays, phase II enzyme induction testing was also conducted to determine if a material had detoxification properties. The phase II enzyme induction assay measures a sample's ability to induce quinone reductase (a phase II enzyme) which is indicative of detoxification events. Broccoli is known as a good phase II enzyme inducer because of its sulforaphane content. Pure sulforaphane has activity at $10^6$ U/g, while broccoli has reported activity from 4000-74,000 U/g (dependent on variety, form, and/or extraction conditions). Activity above 30,000 U/g is considered excellent. Activity less than 5,000 U/g is considered minimal. Most materials that are considered good phase II enzyme inducers will have activity between 15,000-30,000 U/g.

All the blends tested had good to excellent phase II enzyme induction activity. The highest activity came from 8523-27 (Example 8) and the lowest from 8523-31 (Example 4). Excellent activity also came from 8523-22, (Example 7), 8523-23, 8523-30 (Example 3), 8523-32 (Example 5) and 8523-33. Table 10 gives the results of the Phase II Enzyme Induction assay for all samples tested.

TABLE 10

Phase II Enzyme (Quinone Reductase) Induction Assay Results

| Sample Number | Formula Number or Sample Name | U/g | Rank |
|---|---|---|---|
| NF6523 | 8523-20-CI | 23,810 | +++ |
| NF6523 | 8523-21-CI | 24,690 | +++ |
| NF6523 | 8523-22-CI | 51,280 | ++++ |
| NF6523 | 8523-23-CI | 31,750 | ++++ |
| NF6523 | 8523-24-CI | 15,500 | +++ |
| NF6523 | 8523-25-CI | 26,670 | +++ |
| NF6523 | 8523-26-CI | 16,260 | +++ |
| NF6523 | 8523-27-CI | 83,330 | ++++ |
| NF6523 | 8523-28-CI | 19,610 | +++ |
| NF6523 | 8523-30-CI | 44,440 | ++++ |
| NF6523 | 8523-31-CI | 9950 | ++ |
| NF6523 | 8523-32-CI | 47,620 | ++++ |
| NF6523 | 8523-33-CI | 60,600 | ++++ |
|  | Milk Thistle | >100,000 | ++++ |
| CD5439 | King Drink | 17,540 | +++ |

* Inducer units per gram of fresh weight of material.
− = Negligible activity,
+ = Little activity,
++ = Good activity,
+++ = Very good activity,
++++ = Excellent activity.
** Not reportable due to toxicity to cells.

Experimental

Stock sample solutions are made in DMSO, then diluted in cell culture media for testing. Treatment of HepG2 cells (human liver cell line) is done by adding 100 μL of sample to each of three wells of a 96-well microtiter plate. After a 4 hour incubation, the insult is added (2.5% ethanol or 0.2% carbon tetrachloride) and an additional overnight incubation period is conducted. The next day, cell viability is measured using two different assays. First, using the CYTOTOX-ONE™ Homogenous Membrane Integrity Assay by Promega, the number of non-viable cells is estimated by measuring the release of lactate dehydrogenase ("LDH") into the media. LDH leaks out of the cell when the cell membrane is compromised. The second assay is the MTT assay, which measures the reduction of a yellow tetrazolim salt ("MTT") into an insoluble purple formazen product by the mitochondria of viable cells. Following an incubation with the MTT solution, isopropanol is added to solubilize the colored crystals. The amount of color produced is directly proportional to the number of viable cells.

Protection is determined by first calculating a percent toxicity of each well (1-experimental/negative control), after averaging the three replicates. Percent protection is then calculated by the following: (% Toxicity Positive Control–% Toxicity Sample)/% Toxicity Positive Control, the positive control being either 2.5% ethanol or 0.2% carbon tetrachloride. The concentration that exhibits 50% protection (EC-50) can then be assessed. For the purpose of this experiment, this was categorized as either <1, 1, 1-10, 10, 10-100, 100 or >100 μg/mL.

For the Phase II Enzyme Induction Assay, stock sample solutions are made in acetonitrile, then diluted in cell culture media for testing. Treatment of Hepa1c1c7 cells (murine hepatoma cell line) is done by adding 150 μL of sample to each of three wells, in a 96-well microtiter plate. After 48 hours incubation, induction activity of quinone reductase is established by measuring the NADPH-dependent, menadiol-mediated reduction of MTT. Activity is reported as inducer units per gram of fresh weight of material, where one unit of inducer activity is defined as the amount of inducer required to double the quinone reductase specific activity of Hepa1c1c7 cells.

Mammalian Studies

Clinical testing can be conducted to confirm the efficacy of the formulations on liver health. It is expected that the formulations will improve liver health by protecting the liver from chemical and alcohol insults. A protocol for such testing follows.

Protocol 1: $CCl_4$ Liver Injury Model 1.1 Principles.

When $CCl_4$ is activated by microsomal enzyme of liver, trichloromethane free radicals ($CCl_3$.) are formed. Covalent combination of this free radical with protein results in impairment of protein synthesis and disorder of lipid catabolism, causing accumulation of triglyceride (TG) in liver cells. $CCl_3$. also can combine with $O_2$ rapidly to form trichloromethane peroxide free radicals ($CCl_3O_2$.), leading to lipid peroxidation which causes degenerative injury of cell membrane, leakage of enzymes and various types of pathological changes of cells and even necrosis.

1.2 Experimental Animals.

Adult rats or mice of single sex. Each group consists of 8-12 rats (180-220 g) or 10-15 mice (18-22 g).

1.3 Experimental Methods and Procedures.

1.3.1 Dosage Groups and Duration of Administration of the Test Sample.

Three dosage groups, one blank control group and one model control group are set. The dosage of one of the dosage groups is 10 times (mice) or 5 times (rats) the recommended human dosage. $CCl_4$ (analytically pure) is used to form liver injury model. The method of forming model can use intragastric administration or intraperitoneal injection. The concentration of $CCl_4$ for intragastric administration in mice is 1%. $CCl_4$ is diluted with edible vegetable oil and the dosage for intragastric administration is 5 mL/kg BW (the dosage in terms of $CCl_4$ is 80 mg/kg BW). The concentration of $CCl_4$ for intragastric administration in rats is 2%-3% and the dosage is 5 mL/kg BW (the dosage in terms of $CCl_4$ is 160-240 mg/kg BW). Positive control group and solvent control group may be set if necessary. The duration of administration of the test sample is 30 days and can be prolonged to 45 days if necessary.

1.3.2 Route of Administration of the Test Sample.

The test sample is given intragastrically. If this is impossible, the test sample can be mixed into the feed or drinking water and the feed intake or water drunk is recorded.

1.3.3 Experimental Procedures.

The animals of the experimental group are given intragastrically the test sample daily, while those of the blank control group and the model control group are given distilled water. The animals are weighed twice a week for adjusting the dosage of the test sample. On the eve of day 30 of the experiment, the animals of various groups fast for 16 h. The animals of the model group and various test sample groups are given intragastrically single dose of $CCl_4$, while those of the blank control group are given vegetable oil. The animals of the experimental group continue to receive the test sample until the end of the experiment (the interval between administration of the test sample and $CCl_4$ is over 4 h). After giving $CCl_4$, the animals are sacrificed 24 h or 48 h later according to the actual conditions. Blood is taken and serum is separated for measuring ALT and AST. Liver is taken for histopathological examination.

1.3.4 Indices for Measurement.

Serum glutamate-pyruvate transaminase (ALT), glutamic-oxaloacetic transaminase (AST), histopathological examination of liver.

1.4 Measurement of ALT and AST.

1.4.1 Measuring Method.

Full-automatic biochemical analyzer or Reitman-Frankel method (reagent kit) can be selected.

1.4.1 Data Treatment and Result Assessment.

Variance analysis is used, but variance homogeneity test should be performed first according to the procedures of variance analysis. If the variance is homogeneous, F value is calculated. If F value is $<F_{0.05}$, the conclusion is that the difference between means of different groups is not significant. If F value is $\geq F_{0.05}$ and P is $\leq 0.05$, the method of paired comparison of means between several experimental groups and one control group is used for statistical analysis. For data with abnormal distribution or variance inhomogeneity, appropriate conversion of variables is performed and the converted data are used for statistical analysis after the requirement of normal or variance homogeneity is fulfilled. If the purpose of normal or variance homogeneity is still not achieved after conversion of variables, rank test is used for statistical analysis.

If ALT and AST of the test sample group are different significantly from those of the model control group, the results of ALT and AST can be assessed as positive respectively.

1.5 Histopathological Changes of Liver Diagnostic Criteria and Result Assessment.

1.5.1 Experimental Materials.

The left lobe of rat liver is fixed with 10% formalin. The liver tissue is taken from the cross section of middle part of the left lobe of liver for routine preparation of pathological section (paraffin embedding, H.E. strain).

1.5.2 Microscopic Examination.

Using the 40-fold objective to observe continuously the whole tissue section, the pathological changes of cells are recorded beginning from the visual field of one end of the liver. The degenerative changes of central liver cells of the lobe and necrosis of a few cells can be seen. The main types of pathological changes are ballooning degeneration, fatty degeneration, condensation of cytoplasm, hydropic degeneration and necrosis of liver cells, etc.

1.5.3 Criteria for Rating.

Each pathological change accounting for the portion of area of visual field in each visual field is recorded respectively and the total score of pathological changes in the visual fields observed is added up.

| Ballooning degeneration of liver cells: (swelling of cells, a little cytoplasm remains) | |
|---|---|
| Roughly normal | 0 points |
| Liver cells with ballooning degeneration account for ¼ of whole visual field | 1 point |
| Liver cells with ballooning degeneration account for ½ of whole visual field | 2 points |
| Liver cells with ballooning degeneration account for ¾ of whole visual field | 3 points |
| Liver cells with ballooning degeneration account for whole visual field | 4 points |
| Fatty degeneration of liver cells: (distinctly demarcated fat drop vacuoles appear in cytoplasm of liver cells) | |
| Roughly normal | 0 points |
| Liver cells with fatty degeneration account for ¼ of whole visual field | 1 point |
| Liver cells with fatty degeneration account for ½ of whole visual field | 2 points |
| Liver cells with fatty degeneration account for ¾ of whole visual field | 3 points |
| Liver cells with fatty degeneration account for whole visual field | 4 points |
| Condensation of cytoplasm: (eosinophilic stain is enhanced) | |
| Roughly normal | 0 points |
| Liver cells with condensation of cytoplasm account for ¼ of whole visual field | 1 point |
| Liver cells with condensation of cytoplasm account for ²⁄₄ of whole visual field | 2 points |
| Liver cells with condensation of cytoplasm account for ¾ of whole visual field | 3 points |
| Liver cells with condensation of cytoplasm account for whole visual field | 4 points |
| Hydropic degeneration: | |
| No liver cell with hydropic change is seen | 0 points |
| Liver cells with hydropic degeneration account for ¼ of whole visual field | 1 point |
| Liver cells with hydropic degeneration account for ²⁄₄ of whole visual field | 2 points |
| Liver cells with hydropic degeneration account for ¾ of whole visual field | 3 points |
| Diffuse liver cells with hydropic degeneration account for whole visual field | 4 points |
| Necrosis of liver cells: (eosinophilic change of cytoplasm, coagulation necrosis) | |
| No necrotic cell is seen | 0 points |
| Sporadic necrotic cells account for ¼ of whole visual field | 1 point |
| Necrotic cells account for ²⁄₄ of whole visual field | 2 points |
| Necrotic cells account for ¾ of whole visual field | 3 points |
| Diffuse necrotic cells account for whole visual field | 4 points |

1.5.4 Data Treatment and Result Assessment.

Variance analysis is used, but variance homogeneity test should be performed first according to the procedures of variance analysis. If the variance is homogeneous, F value is calculated. If F value is $<F_{0.05}$, the conclusion is that the difference between means of different groups is not significant. If F value is $\geq F_{0.05}$ and P is $\leq 0.05$, the method of paired comparison of means between several experimental groups and one control group is used for statistical analysis. For data with abnormal distribution or variance inhomogeneity, appropriate conversion of variables is performed and the converted data are used for statistical analysis after the requirement of normal or variance homogeneity is fulfilled. If the purpose of normal or variance homogeneity is still not achieved after conversion of variables, rank test is used for statistical analysis.

Among the pathological changes of liver cells including ballooning degeneration, fatty degeneration, cytoplasm condensation, hydropic degeneration and necrosis of liver cells, if the necrosis of liver cells in any dosage group of test sample is alleviated as compared with that in the model control group with significant difference and other types of pathological changes are alleviated significantly or have no significant difference as compared with those in the model control group, the results of animal pathological experiment can be assessed as positive.

If aggravation and alleviation of the 4 types of pathological changes of liver cells, namely, ballooning degeneration, fatty degeneration, cytoplasm condensation and hydropic degeneration, are present simultaneously with significant difference and necrosis of liver cells is alleviated in any one dosage group of the test sample with significant difference as compared with the model control group, the scores of various pathological changes and double of necrosis score are added together. The total score is used for statistical analysis. If the total score has significant difference, the results of animal pathological experiment can be assessed as positive.

1.6 Assessment of Results.

It is expected that any one of the two blood biochemical indices, ALT and AST, and the result of pathological examination will be positive and the test sample will be assessed as assisting in the protection against chemical injury to the liver.

Protocol 2: Model of Alcoholic Injury of Liver 2.1 Principles.

After taking large amounts of ethyl alcohol, massive dehydroxylation catalyzed by ethanol dehydrogenase causes disorder of tricarboxylic acid cycle and weakening of oxidation of fatty acid, thereby influencing fat metabolism and precipitation of fat in liver cells. At the same time, ethyl alcohol can activate oxygen molecules and cause production of oxygen free radicals, leading to lipid peroxidation of liver cell membrane and depletion of reduced glutathione in body.

2.2 Experimental Animals.

Adult mice or rats of single sex. Each group consists of 8-12 rats (180-220 g) or 10-15 mice (18-22 g).

2.3 Experimental Methods and Procedures.

2.3.1 Dosage Groups and Duration of Administration of the Test Sample.

Three dosage groups, one blank control group and one model control group are set. The dosage of one of the dosage groups is 10 times (mice) or 5 times (rats) the recommended human dosage. A positive control group may be set if necessary. Absolute ethyl alcohol (analytically pure) is used to form model of liver injury. The concentration of absolute ethyl alcohol is 50% (diluted with distilled water) and the dosage for intragastric administration to mice is 12-14 mL/kg BW (equivalent to ethyl alcohol 6000-7000 mg/kg BW). The duration of administration of the test sample is 30 days and can be prolonged to 45 days if necessary.

2.3.2 Route of Administration of the Test Sample.

The test sample is given intragastrically. If intragastric administration is impossible, the test sample can be mixed in feed or drinking water, and the feed intake and drinking water drunk of each animal is recorded.

2.3.3 Experimental Procedures.

The animals of the test sample groups are given intragastrically the test sample every day and those of the blank control group and model control group are given distilled water. The animals are weighed twice weekly and the dose of the test sample is adjusted according to body weight. At the time of completion of administration of the test sample, a single dose of 50% ethyl alcohol 12 mL/kg BW is given to the animals of the model control group and three dosage groups, while the animals of the blank control group are given distilled water. After fasting for 16 h, the animals are sacrificed for examination of various indices and histopathological examination.

2.3.4 Indices for Examination.

Malondialdehyde (MDA), reduced glutathione (GSH), triglyceride (TG) content of liver.

2.4 Method for Measuring the Degradation Product of Lipid Peroxide Malondialdehyde (MDA) in Liver Homogenate.

2.4.1 Principle.

MDA is one of the final products of peroxidation of lipids of cell membrane. Measuring MDA content can estimate indirectly the degree of lipid peroxidation. When MDA and thiobarbital are heated together in acidic condition, pink-colored complex is formed and its absorption peak is at 535 nm, from which the MDA content can be measured.

2.4.2 Instruments and Reagents.

Instruments: 721 spectrophotometer, sample micro-applicator, thermostat water bath, ordinary centrifuge, mixing rotator, centrifuge tube with stopper, tissue homogenizer.

Reagents: 0.2M acetate buffer solution, pH 3.5:

| | |
|---|---|
| 0.2 M acetic acid solution | 185 mL |
| 0.2 M sodium acetate solution | 15 mL |

1 mmol/L tetraethoxyl propane (stock solution, kept at 4° C. for 3 months), diluted with water to 40 nmol/mL just before use:

8.1% sodium dodecyl sulfate SDS
0.8% thiobarbital TBA
0.2 M phosphate buffer solution, pH 7.4
    0.2 M disodium hydrogen phosphate 1920 mL
    0.2 M potassium dihydrogen phosphate 480 mL 2.4.3 Experimental Procedures.

2.4.3.1 Preparation of Sample.

Tissue homogenate sample: certain quantity of the organ needed is rinsed with normal saline, wiped to dry, weighed, minced and put into homogenizer. 0.2 M phosphate buffer solution is added and the mixture is homogenized at 2000 r/min for 10 s. The centrifugation is repeated 3 times with 30 s intervals to form 5% tissue homogenate (W/V). The homogenate is centrifugalized at 3000 r/min for 5-10 min and the supernatant is taken for measurement.

2.4.3.2 Measurement of the Sample.

| Reagent | Blank tube | Sample tube | Standard tube |
|---|---|---|---|
| 5% tissue homogenate | | 0.1 mL | |
| 40 nmol/mL tetraethoxyl propane | | | 0.1 mL |
| 8.1% SDS | 0.2 mL | 0.2 mL | 0.2 mL |
| 0.2 M acetate buffer solution | 1.5 mL | 1.5 mL | 1.5 mL |
| 0.8% TBA | 1.5 mL | 1.5 mL | 1.5 mL |
| H$_2$O | 0.8 mL | 0.7 mL | 0.7 mL |

Mix to homogenize, boiling water bath for 60 min protect from light, cooled with flowing water, colorimetry at 532 nm 2.4.3.3 Calculation.

Lipid peroxide content (nmol/mg tissue) =
$$\frac{B-A}{F-A} \times C \times K = \frac{B-A}{F-A} \times 40 \times \frac{1}{0.05 \times 1000}$$

Lipid peroxide content (nmol/100 mg protein) =
$$\frac{B-A}{F-A} \times C \times K = \frac{B-A}{F-A} \times 40 \times \frac{1}{0.05} \times \frac{1}{\text{Protein (mg)/g tissue}} \times 100$$

A: absorbance of blank tube
B: absorbance of sample tube
F: absorbance of tetraethoxyl propane
C: concentration of tetraethoxyl propane (40 nmol/mL)
K: multiple of dilution 2.4.3.4 Data Treatment and Result Assessment.

The data are analyzed with variance analysis, but variance homogeneity test should be performed first according to the procedures of variance analysis. If the variance is homogeneous, F value is calculated. If F value is $<F_{0.05}$, the conclusion is that the difference between means of different groups is not significant. If F value is $\geq F_{0.05}$ and P is $\leq 0.05$, the method of paired comparison of means between several experimental groups and one control group is used for statistical analysis. For data with abnormal distribution or variance inhomogeneity, appropriate conversion of variables is performed and the converted data are used for statistical analysis after the requirement of normal or variance homogeneity is fulfilled. If the purpose of normal or variance homogeneity is still not achieved after conversion of variables, rank test is used for statistical analysis.

Assessment of Results

It is expected that the MDA content of test sample groups will be significantly different from that of the model control group and, as such, the result of this index will be assessed as positive.

2.5 Method for Measuring Reduced Glutathione (GSH) in Liver Homogenate.

2.5.1 Principle.

Reaction between GSH and 5,5'-dithionitroformic acid (DTNB) catalyzed by GSH-Px produces yellow-colored 5-thio-2-nitro-formic acid anion which has maximum absorption peak at wavelength of 423 nm. Measuring the concentration of this ion can calculate GSH content.

2.5.2 Reagents.

| | |
|---|---|
| 0.9% normal saline | |
| 4% sulfosalicylic acid solution | |
| 0.1 mol/L PBS solution (pH = 8.0) | |
| $Na_2HPO_4$ | 13.452 g |
| $KH_2PO_4$ | 0.722 g |
| Distilled water | ad 1000 mL. |

0.004% DTNB solution: DTNB 40 mg is dissolved in 1000 mL of 0.1 mol/L PBS solution (pH=8.0).

Sodium azide buffer solution.

| | |
|---|---|
| $NaN_3$ | 16.25 mg |
| $EDTA-Na_2$ | 7.44 mg |
| $Na_2HPO_4$ | 1.732 g |
| $NaH_2PO_4$ | 1.076 g |

Distilled water ad 1000 mL. Small amount of HCl and NaOH are used to regulate pH 7.0.

The solution is kept at 4° C.

Standard solution: Reduced GSH 15.4 mg is weighed and sodium azide buffer solution is added to 50 mL to make the final concentration 1 mmol/L. The solution is prepared just before use.

2.5.3 Methods.

2.5.3.1 Measurement of Sample.

Normal saline 5 mL is added to liver 0.5 g. The mixture is well ground to form fine thick liquid (10% liver homogenate). After homogenizing, 4% sulfosalicylic acid 0.5 mL is added to the homogenate 0.5 mL. After mixing, the mixture is centrifugalized at 300 rpm for 10 min at room temperature and the supernatant is the sample.

| Reagent | Tube for measurement | Blank tube |
|---|---|---|
| Sample | 0.5 mL | — |
| 4% sulfosalicylic acid | — | 0.5 mL |
| DINB | 4.5 mL | 4.5 mL |

The mixture is mixed, laid aside for 10 min at room temperature and its absorbance is measured at 412 nm.

2.5.3.2 Standard Curve.

| | Reagent | | | | | |
|---|---|---|---|---|---|---|
| | 1 | 2 | 3 | 4 | 5 | 6 |
| 1 mmol/L GSH (mL) | 0 | 0.05 | 0.10 | 0.15 | 0.20 | 0.25 |
| Normal saline (mL) | 0.50 | 0.45 | 0.40 | 0.35 | 0.20 | 0.25 |
| DTNB (mL) | 4.50 | 4.50 | 4.50 | 4.50 | 4.50 | 4.50 |
| GSH content ($\mu mol/L$) | 0 | 100 | 200 | 300 | 400 | 500 |

2.5.3.3 Calculation.

Sample GSH content ($\mu mol/L$ liver tissue)=corresponding curve concentration value ($\mu mol/L$)÷50 g/L 2.5.4 Data Treatment and Result Assessment.

The data are analyzed with variance analysis, but variance homogeneity test is performed first according to the procedures of variance analysis. If the variance is homogeneous, F value is calculated. If F value is <$F_{0.05}$, the conclusion is that the difference between means of different groups is not significant. If F value is $\geq F_{0.05}$ and P is $\leq 0.05$, the method of paired comparison of means between several experimental groups and one control group is used for statistical analysis. For data with abnormal distribution or variance inhomogeneity, appropriate conversion of variables is performed and the converted data are used for statistical analysis after the requirement of normal or variance homogeneity is fulfilled. If the purpose of normal or variance homogeneity is still not achieved after conversion of variables, rank test is used.

Assessment of Results

It is expected that the reduced GSH content of the test sample group will be significantly different from that of the model control group and, as such, the result of this index is assessed as positive.

2.6 Method for Measuring Triglyceride (TG) in Liver Homogenate.

2.6.1 Measuring Method.

Triglyceride measurement reagent kit (glycerophosphoric acid oxidase peroxidase method) is used to measure the triglyceride content in 10% liver homogenate. Same as the method of measuring serum triglyceride, equal amount of 10% liver homogenate is used instead of serum and the measurement is performed according to the description of operation. The result of measurement is expressed as mmol/g liver weight.

2.6.2 Data Treatment and Result Assessment.

The data are treated with variance analysis, but variance homogeneity test is performed first according to the procedures of variance analysis. If the variance is homogeneous, F value is calculated. If F value is <$F_{0.05}$, the conclusion is that the difference between means of different groups is not significant. If F value is $\geq F_{0.05}$ and P is $\leq 0.05$, the method of paired comparison of means between several experimental groups and one control group is used for statistical analysis. For data with abnormal distribution or variance inhomogeneity, appropriate conversion of variables is performed and the converted data are used for statistical analysis after the requirement of normal or variance homogeneity is fulfilled. If the purpose of normal or variance homogeneity is still not achieved after conversion of variables, rank test is used for statistical analysis.

Assessment of Results

It is expected that the TG of the test sample group will be significantly different from that of the model control group and, as such, the result of this index will be assessed as positive.

2.7 Histopathological Chances of Liver, Diagnostic Criteria and Result Assessment.

2.7.1 Experimental Materials.

Cross section at middle part of left lobe of liver is performed for taking examination material. Frozen section is made and stained with Sudan III staining.

2.7.2 Microscopic Examination.

The pathological changes of the cells are recorded beginning from the visual field at one end of the liver. 40-fold objective is used for continuous observation of whole tissue section. The main objects for observation are distribution, range and area of fat drops in liver.

2.7.3 Criteria for Rating.

| | |
|---|---|
| The fat drops in liver cells are sporadic and scarce | 0 points |
| The liver cells containing fat drops do not exceed ¼ | 1 point |
| The liver cells containing fat drops do not exceed ½ | 2 points |
| The liver cells containing fat drops do not exceed ¾ | 3 points |
| The liver tissue is almost replaced by fat drops | 4 points |

2.7.4 Data Treatment and Result Assessment.

Variance analysis is used, but variance homogeneity test should be performed first according to the procedures of variance analysis. If the variance is homogeneous, F value is calculated. If F value is $<F_{0.05}$, the conclusion is that the difference between means of different groups is not significant. If F value is $\geq F_{0.05}$ and P is $\leq 0.05$, the method of paired comparison of means between several experimental groups and one control group is used for statistical analysis. For data with abnormal distribution or variance in homogeneity, appropriate conversion of variables is performed and the converted data are used for statistical analysis after the requirement of normal or variance homogeneity is fulfilled. If the purpose of normal or variance homogeneity is still not achieved after conversion of variables, rank test is used for statistical analysis.

It is expected that the fatty degeneration in any dosage group of test sample will be alleviated as compared with the model control group with statistical difference and, as such, the result will be assessed as positive.

2.8 Assessment of the Results.

It is expected that the following conditions will be fulfilled and, as such, the test sample would be assessed as assisting in protection against alcoholic liver injury:

(a) The results of examination of 3 indices, namely, liver MDA, reduced GSH and TG, are positive.

(b) Any two of the 3 indices, namely, liver MDA, reduced GSH and TG, are positive and the results of histopathological examination are positive.

What is claimed is:

1. A method of inducing phase II enzymes comprising providing 1710 mg-1960 mg of a composition comprising 150 mg-500 mg of wasabi root fiber powder, 200 mg-1000 mg of artichoke leaf extract, and 100 mg-500 mg of notoginseng extract, wherein the composition has phase II enzyme induction activity.

2. The method of claim 1, wherein the composition further comprises 150 mg-1000 mg schisandra berry extract, and 20 mg-500 mg spinach dehydrate.

3. The method of claim 1, wherein the composition further comprises 150 mg-1000 mg kudzu root, and 20 mg-500 mg oregano.

4. The method of claim 1, wherein the composition further comprises 150 mg-1000 mg kudzu root, and 20 mg-500 mg spinach dehydrate.

* * * * *